United States Patent
Puthiaparampil et al.

(10) Patent No.: US 9,115,128 B2
(45) Date of Patent: Aug. 25, 2015

(54) COMPOUNDS OF 3-(5-SUBSTITUTED OXY-2, 4-DINITROPHENYL)-2-OXO-PROPIONIC ACID ESTER, SYNTHESIS AND APPLICATIONS THEREOF

(71) Applicant: ANTHEM BIOSCIENCES PVT. LTD, Bangalore (KR)

(72) Inventors: Tom Thomas Puthiaparampil, Bangalore (IN); Ganesh Sambasivam, Bangalore (IN); Rajulu Gavara Govinda, Bangalore (IN); Ravindra Chandrappa Koramangala, Bangalore (IN)

(73) Assignee: ANTHEM BIOSCIENCES PVT. LTD., Bangalore (IN)

( * ) Notice: Subject to any disclaimer, the term of this patent is extended or adjusted under 35 U.S.C. 154(b) by 0 days.

(21) Appl. No.: 14/218,244

(22) Filed: Mar. 18, 2014

(65) Prior Publication Data

US 2014/0364613 A1     Dec. 11, 2014

(30) Foreign Application Priority Data

Jun. 6, 2013   (IN) .......................... 2466/CHE/2013

(51) Int. Cl.
  *C07D 471/00* (2006.01)
  *C07D 471/04* (2006.01)
  *C07C 205/56* (2006.01)
  *C07C 201/08* (2006.01)

(52) U.S. Cl.
  CPC ............ *C07D 471/04* (2013.01); *C07C 201/08* (2013.01); *C07C 205/56* (2013.01)

(58) Field of Classification Search
  CPC ..................................................... C07D 471/04
  USPC ........................................................... 546/84
  See application file for complete search history.

*Primary Examiner* — Nizal Chandrakumar
(74) *Attorney, Agent, or Firm* — Geeta Kadambi; Riddhi IP LLC (57) ABSTRACT

Synthesis of the novel compound 3 (3-(5-substituted Oxy-2, 4-dinitro-phenyl)-2-oxo-propionic acid ester) to make Pyrroloquinoline quinone (PQQ) and using it for pharmaceutical purposes is described. More specifically, this disclosure relates to synthesizing the PQQ in an efficient method by using a novel intermediate Formula 1 resulting in a shorter process and higher yield of PQQ. A unique process to make sodium compound of PQQ using either sodium hydroxide and/or sodium carbonate is also shown.

5 Claims, 2 Drawing Sheets

COMPOUNDS OF 3-(5-SUBSTITUTED OXY-2, 4-DINITROPHENYL)-2-OXO-PROPIONIC ACID ESTER, SYNTHESIS AND APPLICATIONS THEREOF

CROSS REFERENCE TO RELATED APPLICATION

The instant application claims priority to Indian Provisional Application 2466/CHE/2013, filed on Jun. 6, 2013. The pending Indian Provisional Application 2466/CHE/2013 is hereby incorporated by reference in its entireties for all of its teachings.

FIELD OF TECHNOLOGY

This disclosure relates generally to synthesis and method of making the novel compound 3-(5-substituted Oxy-2,4-dinitro-phenyl)-2-oxo-propionic acid ester. More specifically, this disclosure relates to synthesizing the PQQ in a process efficient method by using a novel intermediate 3-(5-substituted Oxy-2,4-dinitro-phenyl)-2-oxo-propionic acid ester resulting in a shorter process and higher yield of PQQ.

BACKGROUND

Pyrroloquinoline quinone (PQQ) is a natural product and is also known as methoxatin. Among many applications, primary use of PQQ is to protect mitochondria from oxidative stress, providing neuroprotection and cardioprotection. Common food sources of PQQ are parsley, green pepper, green tea, papaya, kiwi and milk. However, the available concentrations of PQQ in the food sources are only in picomolar (pM) to nanomolar (nM) levels. This necessitates the development of chemical processes which can produce large quantities of PQQ for everyday consumption.

The first complete synthesis of PQQ was reported by Corey et al. (1981). As per the Corey's publication, PQQ was synthesized in milligram (mg) scale and the numbers of steps involved in the synthesis of PQQ from commercially available starting material were ten.

Later, the synthesis of PQQ by a nine step-method was reported by Martin et al. (1993). However, the synthetic route described here is very similar to the aforementioned Corey's method and isolation of the final compound involves very complex and laborious process.

Kempf et al., (WO2006/102642A1) describes the synthesis of PQQ. This application mainly discloses the large scale synthesis of PQQ via a combination of Corey's and Martin's route. This application further claims the purification of final compound with sulphuric acid. However, the synthesis method involves large number of steps and the isolation of advanced intermediates further involves tedious labor intensive procedures. Hence, it can be observed that there is a need for better and simpler synthetic method for obtaining Pyrroloquinoline quinone (PQQ).

SUMMARY

The present disclosure, in one embodiment, compound of Formula I and method of making the same is disclosed. Compound of Formula I has numerous applications, such as, in the preparation of pyrroloquinoline quinone (PQQ) and its pharmaceutically acceptable salt. In brief, the synthesis of PQQ and its pharmaceutically acceptable salt using the compound of Formula I as an intermediate is represented below:

Wherein, R1 and R2 is individually selected from a group comprising of hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and each of them can be optionally substituted. The said method of making PQQ further requires minimum number of steps and have improved efficiency and scalability along with many other advantages.

In one embodiment, a process of synthesizing PQQ is performed in six steps.

In one embodiment, the method of making novel 3-(5-substituted oxy-2,4-dinitro-phenyl)-2-oxo-propionic acid ester. In one embodiment, synthesis of PQQ and its sodium salts using Formula III (1 is also used in the above equation to denote Formula II and 3 to denote a form of Formula 1) are described.

Accordingly, the present disclosure relates to a compound of Formula I

Formula I wherein, R1 and R2 are individually selected from a group comprising hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted, or salts thereof;

A process of obtaining a compound of Formula I:

Formula I wherein, R1 and R2 are individually selected from a group comprising hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted, said process comprising reacting a compound of Formula III with ester and base to obtain the compound of Formula I:

Formula III wherein R3 is selected from a group comprising, but not limited to, fluoro, chloro, bromo, iodo, methanesulfonyloxy, toluenesulfonyloxy, trifluoromethanesulfonyloxy, alkyloxy, aryloxy, arolkyl oxy, heteroaryloxy and wherein each of them may be optionally substituted;

A process for preparing 4,5-Dioxo-4,5-dihydro-1H-pyrrolo[2,3-f]quinoline-2,7,9-tricarboxylic acid and salts thereof, said process comprising steps of:

a. reacting a compound of Formula II with nitration mixture to obtain a compound of Formula III

Formula II

Formula III wherein, R3 is selected from a group comprising, but not limited to, fluoro, chloro, bromo, iodo, methanesulfonyloxy, toluenesulfonyloxy, trifluoromethanesulfonyloxy, alkyloxy, aryloxy, arolkyl oxy, heteroaryloxy and wherein each of them may be optionally substituted;

b. reacting the compound of Formula III with ester and base to obtain a compound of Formula I Formula I wherein, R1 and R2 are individually selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted;

c. reacting the compound of Formula I with reducing agent to obtain a compound of Formula IV Formula IV wherein, R1 and R2 are individually selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted;

d. converting the compound of Formula IV to a compound of Formula V in presence of coupling agent Formula V wherein, R1 and R2 are individually selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted; and R4 is selected from group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted;

e. reacting the compound of Formula V with oxidizing agent to obtain a compound of Formula VI Formula VI wherein R2 is selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted; and R4 is selected from group comprising hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted; and f. hydrolyzing the compound of Formula VI to obtain 4,5-Dioxo-4,5-dihydro-1H-pyrrolo[2,3-f]quinoline-2,7,9-tricarboxylic acid and salts thereof; and use of compound of Formula I or salts thereof for preparation of 4,5-Dioxo-4,5-dihydro-1H-pyrrolo[2,3-f]quinoline-2,7,9-tricarboxylic acid and corresponding salts.

In one embodiment, the novel truncated method of synthesis uses a novel intermediate compound 3 (3-(5-substituted Oxy-2,4-dinitro-phenyl)-2-oxo-propionic acid ester). In another embodiment, the intermediate compound 3 is synthesized in two steps using 3-fluoro toluene 1

In one embodiment, a series of 6 steps are used to synthesize PQQ. In one embodiment, the starting material for step 1 is 1-fluoro-3-methyl-benzene at specific concentration which is added to a nitration mixture at a specific concentration and temperature and at a specific time in reaction 1. To obtain compound 2 by reaction 1 by cooling the mixture of reaction 1 to obtain a precipitate 1. Precipitate 1 is further filtered, dried under vacuum and washed with hexane to remove the impurities and as purified compound 2 used for step 2.

In another embodiment, compound 2 is suspended in a solvent (such as methanol) and reacted with sodium methoxide and diethyl oxalate at a special temperature and special concentration to yield intermediate compound that is novel and annotated as compound 3 in the instant specification. In one exemplary example, the chemical name for the compound 3 is 3-(5-methoxy-2,4-dinitro-phenyl)-2-oxo-propionic acid methyl ester.

In one embodiment, compound 3 is reacted with 10% Pd/C in a mixture of dicholoromethane and methanol in a specific ratio under a hydrogen atmosphere to obtain compound 4. In another embodiment, as described in detail in detailed description section, a series of reactions are performed with specific chemical and compound 4 dissolved in dicholoromethane to obtain compound 5. In another embodiment, compound 6 was obtained by dissolving compound 5 in acetonitrile and reacting with a series of solutions having a specific concentration and time period, as stated in detailed description of this application. In one embodiment, the compound 3 as a novel starting material to make compound 4 and compound 5 and compound 6 helps synthesize PQQ in the sixth step.

In one embodiment, Sodium salt of PQQ is made by using sodium carbonate and/or sodium hydroxide.

The compound, process and method of making the novel intermediary compound, PQQ and the sodium salts of the PQQ disclosed herein may be implemented in any means for achieving various aspects, and may be executed to produce PQQ in large scale. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

In the instant invention synthesis of Pyrroloquinoline quinone (PQQ) using a novel intermediate compound 3 (3-(5-substituted Oxy-2,4-dinitro-phenyl)-2-oxo-propionic acid ester) is described herein. The description also discloses a sodium salt of PQQ being synthesized. More specifically the synthesis of the PQQ using the intermediate compound 3 is performed in only six steps to obtain a purer compound in less time and low cost. The instant synthesis of making the PQQ is also less toxic, safe and cost effective. Although the present embodiments have been described with reference to specific example embodiments, it will be evident that various modifications and changes may be made to these embodiments without departing from the broader spirit and scope of the various embodiments.

Materials and Methods:

Chemicals were obtained from multiple commercial suppliers such as Apollo Scientific, Sigma-Aldrich and etc. Final purifications were carried out using Merck silica gel 230-400 mesh. TLC experiments were performed on alumina-backed silica gel 40 F254 plates (Merck, Darmstadt, Germany). The plates were illuminated under UV (254 nm) and $KMnO_4$. Melting points were determined using Buchi B-540 and are uncorrected. All $^1H$ NMR spectra were recorded on a Bruker AM-300 (300 MHz for $^1H$ NMR), Bruker BioSpin Corp., Germany. Molecular weights of unknown compounds were checked by LCMS 6200 series Agilent Technology. Chemical shifts are reported in ppm (δ) with reference to internal standard TMS. The signals are designated as follows: s, singlet; d, doublet; t, triplet; m, multiplet; brs, broad singlet. IR Spectra were recorded using a Bruker Alpha FTIR spectrometer using a diamond ATR single reflectance module (24 scans).

TABLE 1

List of chemicals and their sources:

| Chemical name | Commercial source |
| --- | --- |
| 3-Fluorotoluene | Apollo Scientific |
| Sulphuric acid | Loba Chemie Pvt. Ltd. |
| Nitric acid | Loba Chemie Pvt. Ltd. |
| N-heptane | Rekha chemical corporation |
| Sodium methoxide | Loba Chemie Pvt. Ltd. |
| Methanol | Rekha chemical corporation |
| Diethyl oxalate | SR Drug Laboratories Pvt. Ltd. |
| Dimethyl Glutaconate | Sigma aldrich |
| Ceric ammonium nitrate | Loba Chemie Pvt. Ltd. |
| 10% Pd/C | Johnson Matthey |
| Formic acid | M R Fine Chemical |
| Copper (II) acetate monohydrate | Loba Chemie Pvt. Ltd. |
| Dichloromethane | Rekha chemical corporation |
| Acetonitrile | Rekha chemical corporation |
| Sodium carbonate | Loba Chemie Pvt. Ltd |
| Sodium hydroxide | Loba Chemie Pvt. Ltd. |

Figure 1:
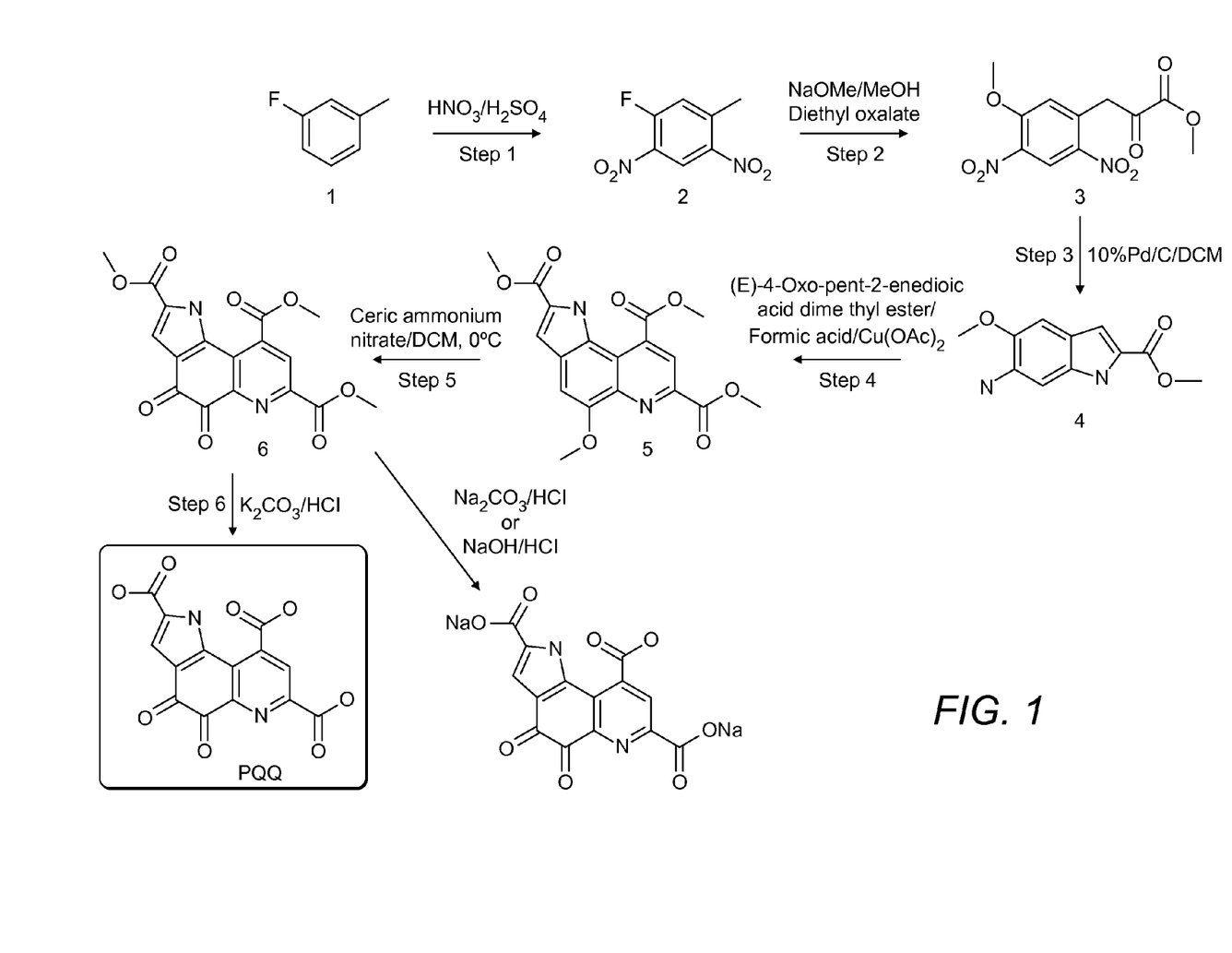
FIG. 1 shows the instant method of synthesizing the PQQ.
Figure 2:
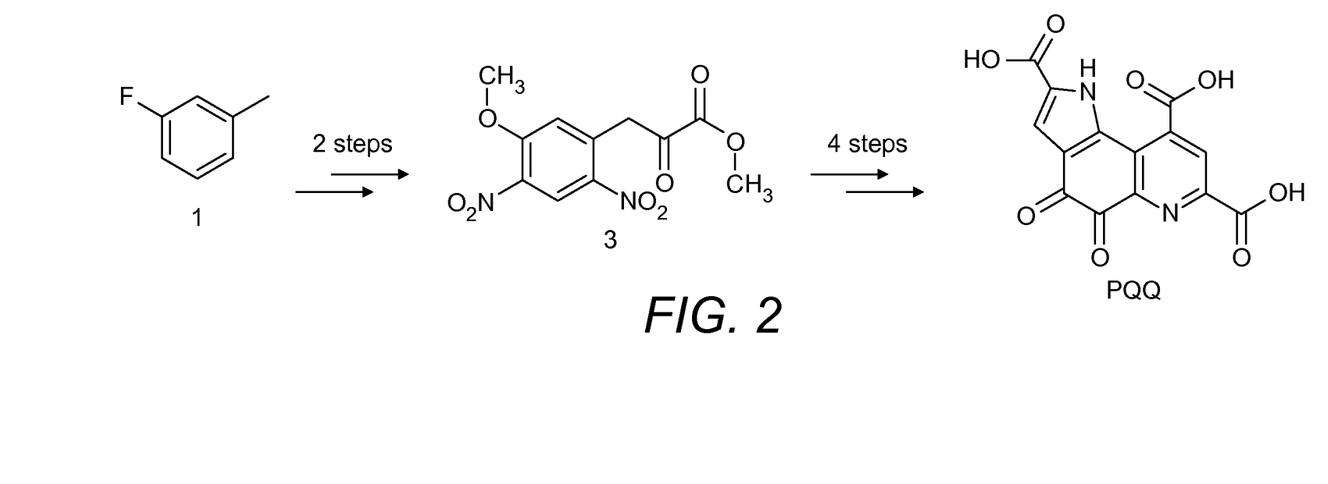
FIG. 2 shows a truncated synthesis path for PQQ formation.

Note:
All the above raw materials are available with multiple commercial suppliers Experimental Procedure:

FIG. 1 shows the intermediate compound 3 that is novel and how PQQ is made in less number of steps. FIG. 2 shows a brief over view of existing starting material and how an intermediate compound 3 is made and subsequently PQQ as a final product.

The present disclosure relates to a compound of Formula I

Formula I wherein, R1 and R2 are individually selected from a group comprising hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted, or salts thereof.

The present disclosure further relates to a process of obtaining a compound of Formula I Formula I wherein, R1 and R2 are individually selected from a group comprising hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted, said process comprising reacting a compound of Formula III with ester and base to obtain the compound of Formula I Formula III wherein R3 is selected from a group comprising, but not limited to, fluoro, chloro, bromo, iodo, methanesulfonyloxy, toluenesulfonyloxy, trifluoromethanesulfonyloxy, alkyloxy, aryloxy, arolkyl oxy, heteroaryloxy and wherein each of them may be optionally substituted.

In an embodiment of the present disclosure, the ester is oxalic acid ester selected from a group comprising dimethyl oxalate, diethyl oxalate, dibenzyl oxalate, diisopropyl oxalate and di-tert-butyl oxalate or any combination thereof; and the base is selected from a group comprising sodium methoxide, sodium ethoxide, potassium t-butoxide, sodium hydride and 1,8-diazabicyclo[5.4.0]undec-7-ene or any combination thereof.

In another embodiment of the present disclosure, the above process is carried out at temperature ranging from about −20° C. to about 100° C., preferably about 0° C. to about 40° C. and for a time period ranging from about 60 minutes to about 72 hours, preferably about 60 minutes to about 16 hours.

In yet another embodiment of the present disclosure, the above process further comprises isolation of the compound of Formula I; and wherein the isolation is carried out by acts selected from a group comprising quenching, filtration and extraction or any combination of acts in any order thereof.

The present disclosure further relates to a process for preparing 4,5-Dioxo-4,5-dihydro-1H-pyrrolo[2,3-f]quinoline-2,7,9-tricarboxylic acid and salts thereof, said process comprising steps of:

a. reacting a compound of Formula II with nitration mixture to obtain a compound of Formula III

Formula II

Formula III wherein, R3 is selected from a group comprising, but not limited to, fluoro, chloro, bromo, iodo, methanesulfonyloxy, toluenesulfonyloxy, trifluoromethanesulfonyloxy, alkyloxy, aryloxy, arolkyl oxy, heteroaryloxy and wherein each of them may be optionally substituted;

b. reacting the compound of Formula III with ester and base to obtain a compound of Formula I Formula I wherein, R1 and R2 are individually selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted;

c. reacting the compound of Formula I with reducing agent to obtain a compound of Formula IV Formula IV wherein, R1 and R2 are individually selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted;

d. converting the compound of Formula IV to a compound of Formula V in presence of coupling agent Formula V wherein, R1 and R2 are individually selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted; and R4 is selected from group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted;

e. reacting the compound of Formula V with oxidizing agent to obtain a compound of Formula VI Formula VI wherein R2 is selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted; and R4 is selected from group comprising hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted; and f. hydrolyzing the compound of Formula VI to obtain 4,5-Dioxo-4,5-dihydro-1H-pyrrolo[2,3-f]quinoline-2,7,9-tricarboxylic acid and salts thereof; and In an embodiment of the present disclosure, the salts as mentioned above are selected from a group comprising glucosamine, sodium, calcium and potassium or any combination thereof.

In an embodiment of the present disclosure, the nitration mixture is selected from a group comprising a mixture of nitric acid and sulphuric acid, calcium nitrate and acetic acid, and tert-butyl nitrite or any combination of mixtures thereof;

the ester is oxalic acid ester selected from a group comprising dimethyl oxalate, diethyl oxalate, Di-tert-butyl oxalate, and diisopropyl oxalate or any combination thereof; the base is selected from a group comprising sodium methoxide, sodium ethoxide, potassium t-butoxide, sodium hydride and 1,8-diazabicyclo[5.4.0]undec-7-ene or any combination thereof; the reducing agent is selected from a group comprising palladium, nickel, sodium dithionite, iron/hydrochloric acid, zinc/acetic acid and tin chloride/hydrochloric acid or any combination thereof; the coupling agent is selected from a group comprising 4-oxo-pent-2-enedioic acid dimethyl ester, 4-oxo-pent-2-enedioic acid diethyl ester, 4-oxo-pent-2-enedioic acid diisopropyl ester and 4-oxo-pent-2-enedioic acid di-tert-butyl ester or any combination thereof; the oxidizing agent is ceric ammonium nitrate; and the hydrolysis is carried out in presence of base selected from a group comprising sodium carbonate, potassium carbonate, sodium hydroxide and lithium hydroxide or any combination thereof.

In an embodiment of the present disclosure, the above process is carried out in presence of solvent selected from a group comprising water, tetrahydrofuran, methanol, ethanol, acetonitrile, dichloromethane, tetrahydrofuran, dimethyl formamide and acetic acid or any combination thereof; and the step (d) is further carried out in presence of acid selected from a group comprising hydrochloric acid, trifluoroacetic acid and p-toluene sulfonic acid or any combination thereof.

In an embodiment of the present disclosure, the above process is carried out at temperature ranging from about −20° C. to about 150° C., preferably about −10° C. to about 100° C. and for a time period ranging from about 30 minutes to about 72 hours, preferably about 30 minutes to about 24 hours.

In an embodiment of the present disclosure, the above process steps (a), (b), (c), (d) (e) and (f) further comprise steps of precipitation or isolation or a combination thereof of the corresponding compound obtained, and wherein the isolation is carried out by acts selected from a group comprising addition of water, quenching, filtration and extraction or any combination of acts in any order thereof.

The present disclosure further relates to use of compound of Formula I or salts thereof for preparation of 4,5-Dioxo-4,5-dihydro-1H-pyrrolo[2,3-f]quinoline-2,7,9-tricarboxylic acid and corresponding salts.

In an object of the present disclosure, compounds of Formula I and salts thereof are provided wherein, said compounds are employed in various applications. Further, the compounds of Formula I serve as industrially useful starting compounds for the efficient synthesis of pharmaceutically significant compounds.

In an exemplary embodiment of the present disclosure, the compounds of Formula I are employed for the synthesis of Pyrroloquinoline quinone (PQQ) and its salts thereof. In particular, the synthetic processes for the preparation of Pyrroloquinoline quinone (PQQ) and its salts involve compounds of Formula I as intermediates. Further, the processes for the preparation of PQQ and the respective salts described in the present disclosure are cost-effective, scalable and efficient.

In an embodiment of the present disclosure, the various chemical compounds and intermediates as disclosed herein are as follows:

Formula I

[3-(5-sustituted oxy-2,4-dinitro-phenyl)-2-oxo-propionic acid esters]

Wherein, R1 and R2 are individually selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted.

Formula II

Wherein, R3 is selected from a group comprising, but not limited to, fluoro, chloro, bromo, iodo, methanesulfonyloxy, toluenesulfonyloxy, trifluoromethanesulfonyloxy, alkyloxy, aryloxy, arolkyl oxy, heteroaryloxy and wherein each of them may be optionally substituted.

Formula III

Wherein, R3 is selected from a group comprising, but not limited to, fluoro, chloro, bromo, iodo, methanesulfonyloxy, toluenesulfonyloxy, trifluoromethanesulfonyloxy, alkyloxy, aryloxy, arolkyl oxy, heteroaryloxy and wherein each of them may be optionally substituted.

Formula IV

Wherein, R1 and R2 are individually selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted.

Formula V

Wherein, R1 and R2 are individually selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted; and R4 is selected from group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted.

Formula VI

Wherein, R2 is selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted; and R4 is selected from group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted.

Pyrroloquinoline quinone (PQQ)

In another embodiment of the present disclosure, the overall synthetic scheme for the preparation of Pyrroloquinoline quinone (PQQ) and its salts comprises the following seven steps:

Method of Synthesizing: Step 1:

Compound of Formula III is prepared by the treatment of compound of Formula II. with a suitable nitration mixture in presence of a suitable solvent at a temperature of about −10° C. to about 80° C. for a time period ranging from about 30 minutes to 48 hours. Preferably, the reaction is carried out at a temperature of about −10° C. to 50° C. for a time period of about 30 min to 2 h.

In an embodiment of the present disclosure, suitable nitration mixture is selected from, but not limited to, a mixture of nitric acid and sulphuric acid, calcium nitrate and acetic acid, tert-butyl nitrite and the likes. Further, suitable solvent for the reaction is selected from, but not limited to, water, acetic acid and the likes. After the completion of reaction, compound of Formula III is isolated by suitable technique such as addition of the reaction mixture to water and filtration of the precipitated compound of Formula III. R3: is selected from a group comprising, but not limited to, fluoro, chloro, bromo, iodo, methanesulfonyloxy, toluenesulfonyloxy, trifluoromethanesulfonyloxy, alkyloxy, aryloxy, arolkyl oxy, heteroaryloxy and wherein each of them may be optionally substituted.

Step 2: The compound of Formula I is directly synthesized by the reaction of compound of Formula III with suitable oxalic acid ester and a suitable base in the presence of solvent at a temperature of about −20° C. to 100° C. for a time-period ranging from about 60 minutes to 72 hours. The reaction is preferably carried out at a temperature of about 0° C. to 40° C. and time-period of about one hour to 36 hours.

In an embodiment of the present disclosure, suitable oxalic acid ester is selected from, but not limited to dimethyl oxalate, diethyl oxalate and the likes. Further, suitable base is selected from, but not limited to sodium methoxide, sodium ethoxide, potassium t-butoxide, sodium hydride, 1,8-diazabicyclo[5.4.0]undec-7-ene and the likes. Additionally, suitable solvent for the reaction is selected from, but not limited to methanol, ethanol, trtrahydro furan, dimethyl formamide and the likes.

In another embodiment, after the completion of reaction, compound of Formula I is isolated by suitable technique such as quenching the reaction mixture with acid, filtration, extraction with solvent or proceeded as such for the next step. Solvent for extraction of the product is selected from, but not limited to esters or halogenated solvents. Preferably, the solvent used is ethyl acetate or dichloromethane.

Wherein, R1 and R2 are individually selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted.

Step 3: Compound of Formula IV is prepared by the treatment of compound of Formula I with a suitable reducing agent in a suitable solvent at a temperature of about −10° C. to 80° C. and for a time-period ranging from about 60 minutes to 72 hours. The reaction is preferably carried out at a temperature of about 0° C. to 50° C. and for a time-period of about one hour to 16 hours.

In an embodiment of the present disclosure, suitable reducing agent is selected from, but not limited to, palladium on carbon or Raney-Nickel or Raney-Nickel/acetic acid under hydrogen pressure, sodium dithionite, iron/hydrochloric acid, zinc/acetic acid, tin chloride/hydrochloric acid, N,N-Dimethylformamide and the likes. Suitable solvent for the reaction is selected from, but not limited to methanol, ethanol, mixture of methanol and dichloromethane and the likes. In another embodiment, after the completion of reaction, compound of Formula IV is isolated by suitable technique such as filtration with solvent or proceeded as such for the next step. Further, solvent for filtration of the product is selected from, but not limited to ethanol, methanol or the likes.

Wherein R1 and R2 are individually selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted.

Step 4 Compound of Formula V is prepared by coupling of compound Formula IV with suitable 4-oxo-pent-2-enedioic acid ester as a coupling agent in the presence of suitable acid in a suitable solvent at a temperature of about −10° C. to 80° C. and for time-period of about 60 minutes to 72 hours. The reaction is preferably carried out at a temperature of about 0° C. to 50° C. and for a time-period ranging from about one hour to 24 hours.

In an embodiment, suitable coupling agent is selected from, but not limited to 4-oxo-pent-2-enedioic acid dimethyl ester, 4-oxo-pent-2-enedioic acid diethyl ester, and the likes. Further, suitable solvent for the reaction is selected from, but not limited to dichloromethane, tetrahydrofuran, acetonitrile and the likes. Suitable acid for the reaction is selected from formic acid, hydrochloric acid, trifluoroacetic acid, p-toluene sulfonic acid and the likes. In another embodiment, after the completion of reaction, compound of Formula V is isolated by suitable technique such as filtration with solvent or proceeded as such for the next step. Suitable catalyst selected from copper acetate and the likes. Further, solvent for filtration of the product is selected from, but not limited to ethanol, methanol and the likes. Suitable catalyst from copper acetate Step 5 Compound of Formula VI is prepared by oxidative demethylation of compound of Formula V with suitable oxidizing agent in a suitable solvent at a temperature of about −10° C. to 80° C. for a time-period of about 30 minutes to 48 hours. The reaction is preferably carried out at a temperature of about −10° C. to 0° C. for time-period of about one hour to 4 hours.

Formula (VI)

In an embodiment, suitable oxidizing agent is selected from, but not limited to ceric ammonium nitrate or the likes. Suitable solvent for the reaction is selected from, but not limited to acetonitrile, dichloromethane, tetrahydrofuran, a mixture of acetonitrile and dichloromethane and the likes. After the completion of reaction, compound of Formula VI is isolated by suitable technique such as filtration with solvent, extraction with solvent or proceeded as such for the next step. Further, solvent for extraction of the product is selected from, but not limited to dichloromethane, chloroform and the likes. Additionally, solvent for filtration of the product is selected from, but not limited to acetonitrile, water and the likes.

Wherein, R2 is selected from a group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted; and R4 is selected from group comprising, but not limited to, hydrogen, straight or branched chain $C_{1-8}$ alkyl, straight or branched chain $C_{1-8}$ alkenyl, straight or branched chain $C_{1-8}$ alkynyl, aralkyl, substituted aralkyl, heteroaralkyl, substituted heteroaralkyl and wherein each of them may be optionally substituted.

Step 6: Compound Pyrroloquinoline quinone (PQQ) is prepared by base hydrolysis of compound of Formula VI with suitable base in a suitable solvent at a temperature of about 10° C. to 150° C. for a time-period ranging from about 60 minutes to 72 hours. The reaction is preferably carried out at a temperature of about 10° C. to 100° C. and for a time-period of about one hour to 24 hours.

4,5-Dioxo-4,5-dihydro-1H-pyrrolo[2,3-f]quinoline-2,7,9-tricarboxylic acid (PQQ)

In an embodiment, suitable base is selected from, but not limited to sodium carbonate, potassium carbonate, sodium hydroxide and the likes. Suitable solvent for the reaction is selected from, but not limited to water, tetrahydrofuran, methanol, ethanol, a mixture of water and ethanol and the likes. After the completion of reaction, compound PQQ is precipitated by quenching the reaction mass with suitable acid such as hydrochloric acid, hydrobromic acid, phosphoric acid and the likes. The precipitated PQQ is isolated by suitable techniques such as filtration with solvent. Solvent for filtration of the precipitated PQQ is selected from, but not limited to acetonitrile, water and the likes.

Step 7: Compound Pyrroloquinoline quinone (PQQ) disodium salt is prepared by base hydrolysis of compound of Formula VI with suitable base in a suitable solvent at a temperature of about 10° C. to 150° C. for a time-period ranging from about 60 minutes to 72 hours. The reaction is preferably carried out at a temperature of about 10° C. to 100° C. and for a time-period of about one hour to 24 hours.

4,5-Dioxo-4,5-dihydro-1H-pyrrolo[2,3-f]quinoline-2,7,9-tricarboxylic acid (PQQ) disodium

In an embodiment, suitable base is selected from, but not limited to sodium carbonate, potassium carbonate, sodium hydroxide and the likes. Suitable solvent for the reaction is selected from, but not limited to water, tetrahydrofuran, methanol, ethanol, a mixture of water and ethanol and the likes. After the completion of reaction, compound PQQ disodium is precipitated by adjusting pH (pH=3.0 to 3.5) of the reaction mass with suitable acid such as hydrochloric acid, hydrobromic acid, phosphoric acid and the likes. The precipitated PQQ disodium is isolated by suitable techniques such as filtration with solvent. Solvent for filtration of the precipitated PQQ disodium is selected from, but not limited to acetonitrile, water and the likes.

The present disclosure is further elaborated with the help of following examples. However, the examples should not be construed to limit the scope of the present disclosure.

EXAMPLES

Example 1

Preparation of 1-fluoro-5-methyl-2,4-dinitro-benzene [Formula III, Wherein R3 is F]

Nitric Acid 67% (about 250 mL, 5.6 mol) is charged to a 3-necked round bottomed flask equipped with mechanical stirrer at a temperature of about 25-30° C. Concentrated sulfuric acid (about 360 mL. 6.75 mol) is thereafter added drop wise at about 0° C. over a period of about 30 minutes. To the obtained nitration mixture, 1-fluoro-3-methyl-benzene [Formula II, wherein R3 is F] (about 100 mL, 0.9 mol) is added drop wise at a temperature ranging about 10-20° C. over a period of about 20 minutes.

The resulting reaction mixture is allowed to stir at a temperature ranging about 20-25° C. over a period of about 30 minutes. Completion of the reaction is monitored by Thin layer Chromatography (TLC). Thereafter, the reaction mixture is poured into crushed ice (about 3.0 L) to precipitate the product. The precipitated product is filtered and dried under vacuum (for about 2 hours). The product obtained is suspended in n-heptane (about 1.0 L) for a wash and filtered. The same heptane wash (about 2×1.0 L) is repeated about twice to remove non polar impurities. The product [1-fluoro-5-methyl-2,4-dinitro-benzene] (about 129 g, 71%) obtained upon filtration is taken to next step. $^1$H NMR (DMSO-d$_6$, 300 MHz): 2.63 (s, 3H), 7.86 (d, J=12.0 Hz, 1H), 8.74 (d, J=6.9 Hz, 1H).

Example 2

Preparation of 3-(5-methoxy-2,4-dinitro-phenyl)-2-oxo-propionic acid methyl ester [Formula I, Wherein R1 is —CH$_3$ and R2 is —CH$_3$]

To a suspension of 1-fluoro-5-methyl-2,4-dinitro-benzene (about 100.0 g, 0.5 mol) in methanol (about 1.5 L), sodium methoxide (about 108 g, 1.9 mol) and diethyl oxalate (about 136 mL, 1.0 mol) are added at a temperature about −10° C. The resulting orange color suspension is slowly allowed to reach a temperature of about 15-20° C. in about 2 hours and continuous stirring is carried out at a temperature of about 15-20° C. over a period of about 32 hours. The reaction mixture is quenched with 1.5 N HCl (about 200 mL), the precipitated solid obtained is filtered and dried under vacuum to obtain the product [3-(5-methoxy-2,4-dinitro-phenyl)-2-oxo-propionic acid methyl ester] as pale yellow solid (about 125 g, 85%). $^1$H NMR (DMSO-d$_6$, 300 MHz): 3.84 & 3.87 (2s, 3H), 4.02 & 4.04 (2s, 3H), 8.63 & 10.93 (s & bs, 2H), 7.56 & 8.07 (2s, 1H), 8.63 & 8.75 (2s, 1H); LC-MS (ESI): 297.0 (M-H).

Example 3

Preparation of 6-amino-5-methoxy-1H-indole-2-carboxylic acid methyl ester [Formula IV, Wherein R1 is —CH$_3$ and R2 is —CH$_3$]

To a solution of 3-(5-methoxy-2,4-dinitro-phenyl)-2-oxo-propionic acid methyl ester (about 100.0 g, 0.32 mol) in a mixture of dichloromethane and methanol (about 1.5 L), 10% Pd/C (about 30 g, 50% wet) is added at about 25° C. The reaction mixture is stirred under hydrogen atmosphere at a temperature of about 25° C. over a period of about 4 hours. The resulting reaction mixture is filtered through celite pad and concentrated under reduced pressure to yield the product [6-amino-5-methoxy-1H-indole-2-carboxylic acid methyl ester] as yellow color solid (about 59 g, 80%).

$^1$H NMR (DMSO-d$_6$, 300 MHz): 3.78 (s, 3H), 3.79 (s, 3H), 4.99 (bs, 2H), 6.62 (s, 1H), 6.90 (s, 1H), 6.92 (s, 1H), 11.90 (s, 1H); LC-MS (ESI): 221.1

Example 4

Preparation of 5-methoxy-1H-pyrrolo[2,3-f]quinoline-2,7,9-tricarboxylic acid trimethyl ester [Formula V, Wherein R1 is —CH$_3$ and R2 is —CH$_3$ and R4 is CH$_3$]

Step 4b | HCOOH/Cu(OAc)₂

To a solution of 6-amino-5-methoxy-1H-indole-2-carboxylic acid methyl ester (about 264.0 g, 1.18 mol) in dichloromethane (about 2.64 L), 4-oxo-pent-2-enedioic acid dimethyl ester (about 227.0 g, 1.3 mol) is added at a temperature of about 25° C. The reaction mixture is allowed to stir at about 25° C. over a period of about 16 hours. Then concentrated the reaction mixture under reduced pressure to minimum volume (500 mL) and precipitated reaction mass with hexane and filtered.

The precipitate obtained upon filtration was dissolved in formic acid (1.2 L), copper(II)acetate monohydrate (119 g, 0.59 mol) was added to the reaction mass allowed to stir at about 25° C. for a period of about 48 hours. Slowly added the reaction mass to water (2.5 L) at 15 to 20° C. and filtered the solids. The solid obtained was washed with mixture of methanol (2.5 L) and aqueous ammonia solution (300 mL) and dried for 12 h at 45 to 50° C. under reduced pressure to obtain the product [5-methoxy-1H-pyrrolo[2,3-f]quinoline-2,7,9-tricarboxylic acid trimethyl ester] as a pale yellow solid (about 350 g, 80%).

Example 5

Preparation of 4,5-dioxo-4,5-dihydro-1H-pyrrolo[2,3-f]quinoline-2,7,9-tricarboxylic acid trimethyl ester [Formula VI, Wherein R2 is —CH₃ and R4 is —CH₃]

To a suspension of 5-methoxy-1H-pyrrolo[2,3-f]quinoline-2,7,9-tricarboxylic acid trimethyl ester (about 250 g, 0.67 mol) in acetonitrile (ACN) (about 7.5 L), a solution of ceric ammonium nitrate (about 1.83 kg, 3.35 mol) in about 2.25 L of water is added over a period of about 30 minutes at about −5° C. The reaction mixture is stirred at about −5° C. over a period of about 1.5 hours. Thereafter, resulting reaction mass is filtered, washed with water and dried to obtain the product [4,5-dioxo-4,5-dihydro-1H-pyrrolo[2,3-f]quinoline-2,7,9-tricarboxylic acid trimethyl ester] as a bright orange solid (about 145 g, 58%). ¹H NMR (DMSO-d₆, 300 MHz): 3.90 (s, 3H), 3.97 (s, 3H), 4.05 (s, 3H), 7.29 (d, J=1.8 Hz, 1H), 8.56 (s, 1H), 12.52 (s, 1H); LC-MS (ESI): 373.0 (M-H).

Example 6

4,5-Dioxo-4,5-dihydro-1H-pyrrolo[2,3-f]quinoline-2,7,9-tricarboxylic acid (PQQ)

K₂CO₃/HCl
Step 6

-continued

PQQ

To a solution of potassium carbonate (about 439 g, 3.18 mol) in water (about 4.5 L), 4,5-dioxo-4,5-dihydro-1H-pyrrolo[2,3-f]quinoline-2,7,9-tricarboxylic acid trimethyl ester (about 200 g, 0.53 mol) is added at about 25° C. The reaction mixture is allowed to stir at about 80° C. over a period of about 12 hours. Completion of reaction is monitored by HPLC. Thereafter, the reaction mixture is acidified (pH: 2.0) with 1N hydrochloric acid to precipitate the product [4,5-Dioxo-4,5-dihydro-1H-pyrrolo[2,3-f]quinoline-2,7,9-tricarboxylic acid] as dark red solid (about 160 g, 91%). $^1$H NMR (DMSO-$d_6$, 300 MHz): 7.21 (s, 1H), 8.60 (s, 1H), 13.42 (s, 1H); LC-MS (ESI): 329 (M-H), Purity by HPLC: 98%.

Example 7

4,5-Dioxo-4,5-dihydro-1H-pyrrolo[2,3-f]quinoline-2,7,9-tricarboxylic acid disodium (PQQ.2Na)

PQQ·2Na

To a solution of 4,5-dioxo-4,5-dihydro-1H-pyrrolo[2,3-f]quinoline-2,7,9-tricarboxylic acid trimethyl ester (1.0 kg, 1 eq, 2.686 moles) in 10% sodium carbonate solution (15 Vol) was heated to 70 to 75° C. over a period of 16 h. Completion of reaction is monitored by HPLC. Thereafter, the reaction mixture is acidified (pH: 3.0-3.5) with 1N hydrochloric acid to precipitate the product [4,5-Dioxo-4,5-dihydro-1H-pyrrolo[2,3-f]quinoline-2,7,9-tricarboxylic acid disodium] as dark red solid (about 0.85 Kg, 85%). $^1$H NMR (D$_2$O, 300 MHz): 6.84 (s, 1H), 8.48 (s, 1H); LC-MS (ESI): 329 (M-H), Purity by HPLC: 98.6%. IR (ATR, cm$^{-1}$) υ: 3407, 1719, 1666, 1621, 1580, 1537, 1497, 1356, 1243, 975 and 731.

Example 8

4,5-Dioxo-4,5-dihydro-1H-pyrrolo[2,3-f]quinoline-2,7,9-tricarboxylic acid disodium (PQQ.2Na)

PQQ·2Na

To a solution of 4,5-dioxo-4,5-dihydro-1H-pyrrolo[2,3-f]quinoline-2,7,9-tricarboxylic acid trimethyl ester (1.0 kg, 1 eq, 2.68 mol) in 3.5% sodium hydroxide solution (15 Vol) was stirred at 25° C. over a period of 3 h. Completion of reaction is monitored by HPLC. Thereafter, the reaction mixture is acidified (pH: 3.0-3.5) with 12N hydrochloric acid over a period of 1 h to precipitate the product [4,5-Dioxo-4,5-dihydro-1H-pyrrolo[2,3-f]quinoline-2,7,9-tricarboxylic acid disodium] as dark red solid (about 0.88 Kg, 88%). $^1$H NMR (D$_2$O, 300 MHz): 6.84 (s, 1H), 8.48 (s, 1H); LC-MS (ESI): 329 (M-H), Purity by HPLC: 99.4%. IR (ATR, cm$^{-1}$) υ: 3423, 2558, 1717, 1674, 1611, 1543, 1502, 1235, 1147, 938 and 718.

Results and Discussion: The PQQ and its salts described herein were synthesized as shown in FIGS. 1 and 2. The nitro toluene 2 was conveniently synthesized from the commercially available (Apollo Scientific Ltd, UK) 3-fluoro toluene as per the reported procedure (Egawa, Hiroshi et al, Journal of Heterocyclic Chemistry, 24(1), 181-5; 1987) and the spectral data of the compound was in agreement with the reported data (Lee, Young B. et al, U.S. Pat. Appl. Publ., 20050187231).

After having synthesized the compound 2, our attention turned towards the synthesis of novel key intermediate 3. Here we have designed a reaction conditions in such way that compound 3 would obtain as a result of three simultaneous reactions [1. Replacing the fluoro with methoxy; 2. Reaction of tolyl with diethyl oxalate and 3. Trans esterification) in one pot. Further reduction of compound 3, would result in compound 4 as result of two simultaneous reactions (1. Reduction of nitro to amine and 2. Formation of indole ring) in one pot.

The reaction of compound 2 with diethyl oxalate in presence of sodium methoxide smoothly yielded a novel intermediate product compound 3 with excellent yield (85%). Formation of the compound 3 was confirmed by its $^1$H NMR and LC-MS data. Reduction of compound 3 with 10% Pd/C under hydrogen pressure obtained indole derivative compound 4. The compound 4 formation was confirmed by its $^1$H NMR and LC-MS data. The advance intermediate 4 was obtained only in three steps.

In prior art (*J. Am. Chem. Soc.* 103 (1981), 5599-5600), ethyl analog of compound 4 was synthesized in seven steps via hazardous reagents/conditions such as diazonium chloride, refluxing the staring materials in acetone in the presence of Dry HCl gas and usage of expensive reagents such as ethyl 2-methylacetoacetate.

Then reaction of compound 4 with (E)-4-Oxo-pent-2-enedioic acid dimethyl ester in the presence of copper acetate and formic acid resulted in quinolone derivative 5 in good yield. $^1$H NMR and LC-MS spectral data confirms the formation of compound 5. Compound 5 analog in prior art was synthesized by using dichloromethane as a solvent and by overnight purging of corrosive dry HCl gas into the reaction container. Further the isolation procedure involved usage of large volumes of dichloromethane and tedious workup procedures (*Helv, Chem, Acta* 76 (1993), 1667, WO2006/102642A1).

Then compound 5 was converted to compound 6 as per the reported protocol (*J. Am. Chem. Soc.* 103 (1981), 5599-5600). After having synthesized pre-final compound 6, our aim was to synthesize PQQ and its slats. Initially we have synthesized PQQ as per the Corey protocol and spectral data of the PQQ obtained via novel intermediate was comparable to literature values (WO2006/102642A1). Later sodium salt of the PQQ was synthesized by base hydrolysis of the compound 6 with sodium carbonate/sodium hydroxide and adjusted the reaction mass pH to 3.0.

Industrial Applicability

The synthesis of PQQ is novel as it uses a novel intermediate compound of Formula I. By employing this novel intermediate, number of steps involved in the synthesis of PQQ is significantly reduced to 6. The disclosed method of synthesis does not involve hazardous and unstable intermediate such as diazonium chlorides, refluxing corrosive HCl gas in acetone as reported in the prior art. Another example, in step 4 of the present synthesis involved usage of formic acid as a solvent. Same step 4 conversion in prior art involves continuous purging of HCl for a period of 10 h. Continues usage of HCl for such a prolonged time would corrode the reaction containers and surrounding environment. The instant synthesis procedure significantly reduces process cycle time, which in turn reduces cost. In conclusion the synthesis procedure is industrially scalable, environment-friendly and safe and very cost effective.

In addition, it will be appreciated that the various synthesis steps, novel intermediate compound and the sodium salts of the PQQ may be embodied using means for achieving the various solvents and salts. Accordingly, the specification and drawings are to be regarded in an illustrative rather than a restrictive sense.

What is claimed is:

1. A compound of Formula I:

wherein, R1 and R2 are individually selected from a group having a straight or branched chain $C_{1-8}$ alkyl and aralkyl.

2. A process of obtaining a compound of Formula I, comprising:

a) reacting 1-fluoro-3-methyl benezene with nitration mixture at 20-30° C. for a period of 30 min to obtain 1-fluoro-5-methyl-2,4-dinitro-benezene (2);

b) and reacting the 1-fluoro-5-methyl-2,4-dinitro-benezene (2) with oxalic acid diester in the presence of base and a solvent at 30-40° C. for a period of about 16 h to 24 h to obtain 3-(5-methoxy-2,4-dinitro-phenyl)-2-oxo-propionic acid methyl ester (3)

3. The process as claimed in claim 2, wherein the nitration mixture in step a) is a mixture of nitric acid and sulphuric acid;

wherein oxalic acid diester in step b) is diethyl oxalate or dimethyl oxalate; wherein the base in step b) is sodium methoxide and wherein the solvent in step b) is methanol.

4. A process for preparing a 4,5-Dioxo-4,5-dihydro-1H-pyrrolo[2,3-f]quinoline-2,7,9-tricarboxylic acid (PQQ) via compound of formula I comprising steps of: a) reacting 1-fluro-3-methyl benzene with nitration mixture at 20-30° C. for a period of 30 min to obtain 1-fluoro-5-methyl-2,4-dinitro-benzene (2);

b) reacting the 1-fluoro-5-methyl-2,4-dinitro-benzene (2) with oxalic acid diester in the presence of base and a solvent at 30-40° C. for a period of about 16 h to 24 h to obtain 3-(5-methoxy-2,4-dinitro-phenyl)-2-oxo-propionic acid methyl ester (3);

(3)

c) reacting the 3-(5-methoxy-2,4-dinitro-phenyl)-2-oxo-propionic acid methyl ester (3) with reducing agent under hydrogen atmosphere in a mixture of dichloromethane and methanol at about 30-40° C. for a period of 4-6 h to obtain 6-amino-5-methoxy-1H-indole-2-carboxylic acid methyl ester (4);

(4)

d) reacting the 6-amino-5-methoxy-1H-indole-2-carboxylic acid methyl ester (4) with 4-oxo-pent-2-enedioic acid dimethyl ester in dichloromethane in the presence of an acid and copper (II) acetate at 20-30° C. for a period of about 16-24 h to obtain 5-methoxy-1H-pyrrolo[2,3-f]quinoline-2,7,9-tricarboxylic acid trimethyl ester (5);

(5)

e) oxidizing the 5-methoxy-1H-pyrrolo[2,3-f]quinoline-2,7,9-tricarboxylic acid trimethyl ester (5) with aqueous ceric ammonium nitrate in a mixture of acetonitrile and dichloromethane at −5 to 25° C. for a period of 1-2 h to obtain 4,5-dioxo-4,5-dihydro-1H-pyrrolo [2,3-f]quinoline-2,7,9-tricarboxylic acid trimethyl ester (6);

(6)

and f) hydrolyzing the 4,5-dioxo-4,5-dihydro-1H-pyrrolo[2,3-f]quinoline-2,7,9-tricarboxylic acid trimethyl ester (6) with a base in water at 20-80° C. for a period of 16 to 24 h to obtain 4,5-dioxo-4,5-dihydro-1H-pyrrolo[2,3-f]quinoline-2,7,9-tricarboxylic acid (PQQ) and salts thereof

PQQ

5. The process as claimed in claim 4, wherein the nitration mixture in step a) is selected from mixture of nitric acid and sulphuric acid;

wherein the oxalic acid diester in step b) is dimethyl oxalate and diethyl oxalate;

wherein the base in step b) is sodium methoxide;

wherein the solvent in step b) methanol;

wherein the reducing agent in step c) is selected from a group consisting of a palladium on charcoal, Raney nickel, sodium dithionite, iron/hydrochloric acid, zinc/acetic acid and tin chloride/hydrochloric acid and combination thereof;

wherein the acid in step d) is selected from formic acid, hydrochloric acid and acetic acid and combination thereof;

wherein the hydrolysis of step 0 is carried out in presence of base selected from a group consisting of a sodium carbonate, potassium carbonate, sodium hydroxide and lithium hydroxide and combination thereof.

* * * * *